US008966956B2

(12) United States Patent
Yoshioka

(10) Patent No.: US 8,966,956 B2
(45) Date of Patent: Mar. 3, 2015

(54) PARTICULATE MATTER AMOUNT DETECTING APPARATUS

(75) Inventor: Mamoru Yoshioka, Susono (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 113 days.

(21) Appl. No.: 13/496,431

(22) PCT Filed: Apr. 30, 2010

(86) PCT No.: PCT/JP2010/057687
§ 371 (c)(1),
(2), (4) Date: Mar. 15, 2012

(87) PCT Pub. No.: WO2011/135717
PCT Pub. Date: Nov. 3, 2011

(65) Prior Publication Data
US 2013/0031954 A1    Feb. 7, 2013

(51) Int. Cl.
*G01N 37/00* (2006.01)
*G01N 1/22* (2006.01)
*G01N 25/00* (2006.01)
*G01N 27/02* (2006.01)
*G01N 15/06* (2006.01)
(Continued)

(52) U.S. Cl.
CPC ............ *G01N 27/02* (2013.01); *G01N 15/0606* (2013.01); *F01N 13/008* (2013.01); *G01N 15/0656* (2013.01); *F01N 2560/05* (2013.01); *G01N 27/041* (2013.01)
USPC ........................................ 73/23.33; 73/28.01

(58) Field of Classification Search
CPC ... G01N 15/02; G01N 15/06; G01N 15/0606; F01N 11/00

USPC ............................................... 73/23.33, 28.01
See application file for complete search history.

(56) References Cited

U.S. PATENT DOCUMENTS

| 5,651,248 A | 7/1997 | Kawamura |
| 7,168,292 B2 * | 1/2007 | Gundel et al. ............... 73/28.01 |

(Continued)

FOREIGN PATENT DOCUMENTS

| JP | A-8-68313 | 3/1996 |
| JP | A-2002-129933 | 5/2002 |
| JP | A-2008-64621 | 3/2008 |

(Continued)

OTHER PUBLICATIONS

A. Messerer, R. Niessner, and U. Pöschl, "Thermophoretic deposition of soot aerosol particles under experimental conditions relevant for modern diesel engine exhaust gas systems" Aerosol Science, vol. 34 (2003) pp. 1009-1021.*

(Continued)

*Primary Examiner* — Lisa Caputo
*Assistant Examiner* — Punam Roy
(74) *Attorney, Agent, or Firm* — Oliff PLC

(57) ABSTRACT

A PM amount detecting apparatus having a PM sensor installed in a sensor case into which a part of exhaust gas of an internal combustion engine allowed to flow through an exhaust gas passage is intaken. The sensor case has a structure which lowers a flow rate of the exhaust gas therein to such an extent that PM is capable of performing thermal phoresis, and a structure which generates therein such a temperature difference that PM is guided to the PM sensor in accordance with the thermal phoresis.

15 Claims, 10 Drawing Sheets

(51) Int. Cl.
*F01N 13/00* (2010.01)
*G01N 27/04* (2006.01)

(56) References Cited

U.S. PATENT DOCUMENTS

2009/0309571 A1  12/2009  Katsuyama et al.
2011/0197571 A1*  8/2011  Visser et al. .................. 60/311

FOREIGN PATENT DOCUMENTS

| JP | A-2008-115765 | 5/2008 |
| JP | A-2008-190502 | 8/2008 |
| JP | A-2010-151554 | 7/2010 |
| WO | WO 2008/117853 A1 | 10/2008 |
| WO | WO 2009/108091 A1 | 9/2009 |

OTHER PUBLICATIONS

C. Berger, H. Horvath, and W. Schindler, "The deposition of soot particles from hot gas streams through pipes," J. Aerosol Sci., vol. 26, No. 2, (1995) pp. 211-217.*

J. Lee, I. Altman, and M. Choi, "Design of thermophoretic probe for precise particle sampling," J. Aerosol Sci., vol. 39 (2008) pp. 418-431.*

D. Lutic, J. Pagels, R. Bjorklund, P. Josza, J. H. Visser, A. W. Grant, M. L. Johansson, J. Paaso, P.-E. Fagerman, M. Sanati, and A. L. Spetz, "Detection of soot using a resistivity sensor device employing thermophoretic particle deposition," J. of Sensors, Hindawi Publishing Corporation, vol. 2010, pp. 1-6.*

M. Lapuerta, F. J. Martos, and J. M. Herreros, "Effect of engine operating conditions on the size of primary particles composing diesel soot agglomerates," J. Aerosol Sci., vol. 38 (2007) pp. 455-466.*

M. Abdolzadeh, M. A. Mehrabian, G. Zahedi, and A. S. Goharrizi, "Effect of thermophoresis and other parameters on the particle deposition on a tilted surface," Int. J. of Heat and Fluid Flow, vol. 32 (2011) pp. 670-679.*

A. Vranos and B. A. Knight, "A gas sampling probe for particulate laden streams," Combustion and Flame, vol. 55 (1984) pp. 121-122.*

G. Kasper, "Hotwire thermal precipitator with low inlet losses and low size selectivity," Rev. of Sci. Instrum., vol. 53(1) (1982) pp. 79-82.*

R. A. Dobbins and C. M. Megaridis, "Morphology of flame-generated soot as determined by thermophoretic sampling," Langmuir, American Chemical Society vol. 3 (1987) pp. 254-259.*

J.-S. Lin and C.-J. Tsai, "Thermophoretic deposition efficiency in a cylindrical tube taking into account developing flow at the entrance region," J. Aerosol Sci., vol. 34 (2003) pp. 569-583.*

International Search Report dated Jul. 27, 2010 in International Application No. PCT/JP2010/057687.

* cited by examiner

PARTICULATE MATTER AMOUNT DETECTING APPARATUS

TECHNICAL FIELD

The present invention relates to a PM amount detecting apparatus for detecting an amount of particulate matter (hereinafter referred to as "PM") contained in an exhaust gas of an internal combustion engine.

BACKGROUND ART

A technique is known, in which a PM amount contained in an exhaust gas of an internal combustion engine is detected by a PM sensor. Patent Document 1 discloses a PM sensor (particulate sensor) provided with at least two electrodes. The PM sensor detects or senses a particulate deposition amount in the PM sensor from the measurement data of the electric characteristic including, for example, the AC impedance between the electrodes. Further, Patent Document 1 describes a technique in which the PM sensor is installed in particulate collecting means which collects PM on a part of a cross section perpendicular to a gas flow passage or on a second flow passage different from the gas flow passage.

Techniques, which relate to PM sensors, are also described in Patent Documents 2 to 5.

PRIOR ART DOCUMENTS

Patent Documents

Patent Document 1: Japanese patent application laid-open No. 2008-064621;
Patent Document 2: Japanese patent application laid-open No. 2008-190502;
Patent Document 3: WO2008/117853A;
Patent Document 4: Japanese patent application laid-open No. 2008-115765;
Patent Document 5: Japanese patent application laid-open No. 08-068313.

SUMMARY OF THE INVENTION

Problem to be Solved by the Invention

In order to detect the PM amount contained in the exhaust gas of the internal combustion engine, a PM sensor is used in some cases, which outputs a signal corresponding to the PM amount deposited or deposited on the sensor itself. The PM sensor as described above is generally installed in an exhaust gas passage. PM contained in the exhaust gas adheres to the PM sensor installed in the exhaust gas passage. Adhered PM is gradually deposited in the PM sensor. The output value of the PM sensor is changed depending on the increase in the PM deposition amount.

As for the PM sensor, PM, which collides with the PM sensor, is adhered to and deposited in the PM sensor. However, PM, which does not collide with the PM sensor, exists in the exhaust gas, and PM, which does not adhere to the PM sensor even when PM collides with the PM sensor, exists in the exhaust gas. When the flow rate of the exhaust gas is raised, the flow rate of PM is increased as well. When the flow rate of PM is increased, then the PM amount itself adhered to the PM sensor is increased, but there is such a tendency that the PM collection ratio in the PM sensor (i.e., ratio of the PM amount adhered to the PM sensor with respect to the flow rate of PM) is lowered. If the PM collection ratio becomes unstable in the PM sensor resulting from the fact as described above, it is feared that it may be difficult to correctly detect the PM amount in the exhaust gas on the basis of the output value of the PM sensor.

The present invention has been made taking the foregoing problem into consideration, an object of which is to provide a technique which makes it possible to detect a PM amount in an exhaust gas of an internal combustion engine more highly accurately.

Means for Solving the Problem

The present invention adopts the following means in order to solve the problem as described above. That is, in the present invention, a PM sensor is installed in a sensor case, and thus it is intended that the flow rate of an exhaust gas is lowered around the PM sensor and PM is guided (introduced or induced) to the PM sensor in accordance with the thermal phoresis.

In particular, the PM amount detecting apparatus according to the present invention resides in a PM amount detecting apparatus which is provided for an exhaust gas passage of an internal combustion engine and which detects an amount of particulate matter contained in an exhaust gas, the PM amount detecting apparatus comprising:

a PM sensor which outputs a signal corresponding to the amount of the particulate matter deposited in the PM sensor itself; and a sensor case which includes the PM sensor installed therein and into which a part of the exhaust gas allowed to flow through the exhaust gas passage is intaken, the sensor case having a structure which lowers a flow rate of the exhaust gas therein to such an extent that the particulate matter is capable of performing thermal phoresis, and a structure which generates therein such a temperature difference that the particulate matter is guided to the PM sensor in accordance with the thermal phoresis.

According to the present invention, the flow rate of the exhaust gas is reduced in the sensor case, and PM is guided (introduced or induced) to the PM sensor in accordance with the thermal phoresis. Accordingly, PM in the exhaust gas tends to adhere to the PM sensor with ease. Therefore, the PM collection ratio can be stably maintained to be high in the PM sensor irrelevant to the flow rate of the exhaust gas in the exhaust gas passage. As a result, the PM amount in the exhaust gas can be detected more highly accurately on the basis of the output value of the PM sensor.

The "structure which lowers the flow rate of the exhaust gas therein to such an extent that the particulate matter is capable of performing the thermal phoresis" of the sensor case according to the present invention can be realized by the installation position and the shape of the sensor case or the position and the shape of the inlet/outlet port for the exhaust gas formed for the sensor case.

For example, the inlet/outlet port for the exhaust gas, which is provided for the sensor case, may be formed in only one direction. Accordingly, the flow of the exhaust gas, which inflows into the sensor case in a certain direction and which outflows into the exhaust gas passage in another direction, can be suppressed in the sensor case. Therefore, the flow rate of the exhaust gas in the sensor case can be lowered to such an extent that the thermal phoresis of PM can be performed. Further, the inlet/outlet port for the exhaust gas may be formed at only an end portion of the sensor case disposed on a downstream side. Accordingly, the influence of the pressure of the main flow of the exhaust gas allowed to flow through the exhaust gas passage is hardly exerted on PM existing in the sensor case. Therefore, PM is subjected to the thermal phoresis more easily.

The "structure which generates therein such a temperature difference that the particulate matter is guided to the PM sensor in accordance with the thermal phoresis" of the sensor case according to the present invention can be realized by the installation position of the sensor case and the installation position of the PM sensor in the sensor case. This structure can be also realized by providing at least any one of a heating device and a cooling device for the sensor case.

The structure as described above may be such a "structure that a temperature of the PM sensor is lowered as compared with a temperature of at least a part of a wall surface of the sensor case". According to this structure, PM contained in the exhaust gas in the sensor case is guided to the PM sensor in accordance with the thermal phoresis. Alternatively, the structure as described above may be such a "structure that the temperature difference is generated between wall surfaces which are opposed to one another while interposing the PM sensor". According to this structure, PM contained in the exhaust gas in the sensor case is moved from the side of the wall surface having a high temperature to the side of the wall surface having a low temperature in accordance with the thermal phoresis. In this situation, the PM sensor is positioned on the route of movement of PM. Therefore, PM is guided to the PM sensor.

In the present invention, for example, the sensor case may be installed so that a part thereof is positioned in the exhaust gas passage and another part is positioned outside the exhaust gas passage. Accordingly, the temperature of the wall surface of the portion of the sensor case positioned outside the exhaust gas passage is lower than the temperature of the wall surface of the portion of the sensor case positioned in the exhaust gas passage. In this arrangement, the PM sensor may be arranged at a portion which is positioned outside the exhaust gas passage in the sensor case. Alternatively, the PM sensor may be arranged at a portion which is positioned in the exhaust gas passage in the sensor case in the vicinity of a position of a wall surface of the exhaust gas passage. Accordingly, the temperature of the PM sensor can be lowered as compared with the temperature of the wall surface of the portion of the sensor case positioned in the exhaust gas passage. Further, it is possible to generate the temperature difference between the wall surfaces of the sensor case which are opposed to one another while interposing the PM sensor.

In the case of the arrangement as described above, it is also allowable to provide a heating device which heats a wall surface of a portion of the sensor case positioned in the exhaust gas passage. Further, in the case of the arrangement as described above, it is also allowable to provide a cooling device which cools a wall surface of a portion of the sensor case positioned outside the exhaust gas passage. According to these arrangements, it is possible to further increase the temperature difference between the wall surfaces of the sensor case or the temperature difference between the wall surface of the sensor case and the PM sensor. As a result, it is possible to accelerate the guided movement (introduction or induction) of PM to the PM sensor in accordance with the thermal phoresis.

The heating device can be realized by providing a heat receiving fin which receives heat of the exhaust gas allowed to flow through the exhaust gas passage, at a portion of the sensor case positioned in the exhaust gas passage. Further, the cooling device can be realized by providing a heat releasing fin which releases heat of the exhaust gas in the sensor case to outside, at a portion of the sensor case positioned outside the exhaust gas passage.

In the present invention, the sensor case may be installed so that at least a part thereof is positioned in the exhaust gas passage. Further, a catalyst, which has an oxidation function, may be provided at a portion positioned in the exhaust gas passage, the portion being a part of an outer wall surface of the sensor case. In this arrangement, the fuel component contained in the exhaust gas, which is allowed to flow through the exhaust gas passage, is oxidized on the catalyst. Therefore, the wall surface of the portion of the sensor case, which is provided with the catalyst, is heated by the heat of oxidation. Therefore, it is possible to lower the temperature of the wall surface of the portion of the sensor case opposed to the portion of installation of the catalyst while interposing the PM sensor, as compared with the temperature of the wall surface of the portion of the sensor case provided with the catalyst. Further, it is possible to lower the temperature of the PM sensor as compared with the temperature of the wall surface of the portion of the sensor case provided with the catalyst.

In the present invention, the sensor case may be provided with a heating device which heats a part of a wall surface of the sensor case. Accordingly, it is possible to lower the temperature of the portion of the wall surface of the sensor case opposed to the heated portion while interposing the PM sensor as compared with the temperature of the portion of the wall surface of the sensor case heated by the heating device. Further, it is possible to lower the temperature of the PM sensor as compared with the temperature of the portion of the wall surface of the sensor case heated by the heating device.

In the case of the arrangement as described above, the sensor case may further include a cooling device which cools a portion of the wall surface thereof opposed to a portion heated by the heating device while interposing the PM sensor. Accordingly, it is possible to further increase the temperature difference between the wall surfaces opposed to one another while interposing the PM sensor. As a result, it is possible to accelerate the guided movement (introduction or induction) of PM to the PM sensor in accordance with the thermal phoresis.

The respective means described above can be combined with each other as far as possible.

Advantageous Effect of the Invention

According to the present invention, it is possible to detect the PM amount contained in the exhaust gas of the internal combustion engine by means of the PM sensor more highly accurately.

EMBODIMENTS FOR CARRYING OUT THE INVENTION

Specified embodiments of the present invention will be explained below on the basis of the drawings. For example, sizes (dimensions), materials, and shapes of constitutive parts or components as well as relative arrangements thereof, which are described in the embodiments of the present invention, are not intended to limit the technical scope of the invention only thereto, unless otherwise specified.

First Embodiment

A first embodiment of the present invention will be explained on the basis of FIGS. 1 to 10. In this embodiment, an explanation will be made about a case in which the present invention is applied in order to detect the PM amount contained in an exhaust gas of a diesel engine for driving a vehicle. The internal combustion engine according to the present invention is not limited to the diesel engine. The internal combustion engine may be a gasoline engine.

[Schematic Arrangement of Exhaust System of Internal Combustion Engine]

Figure 1:
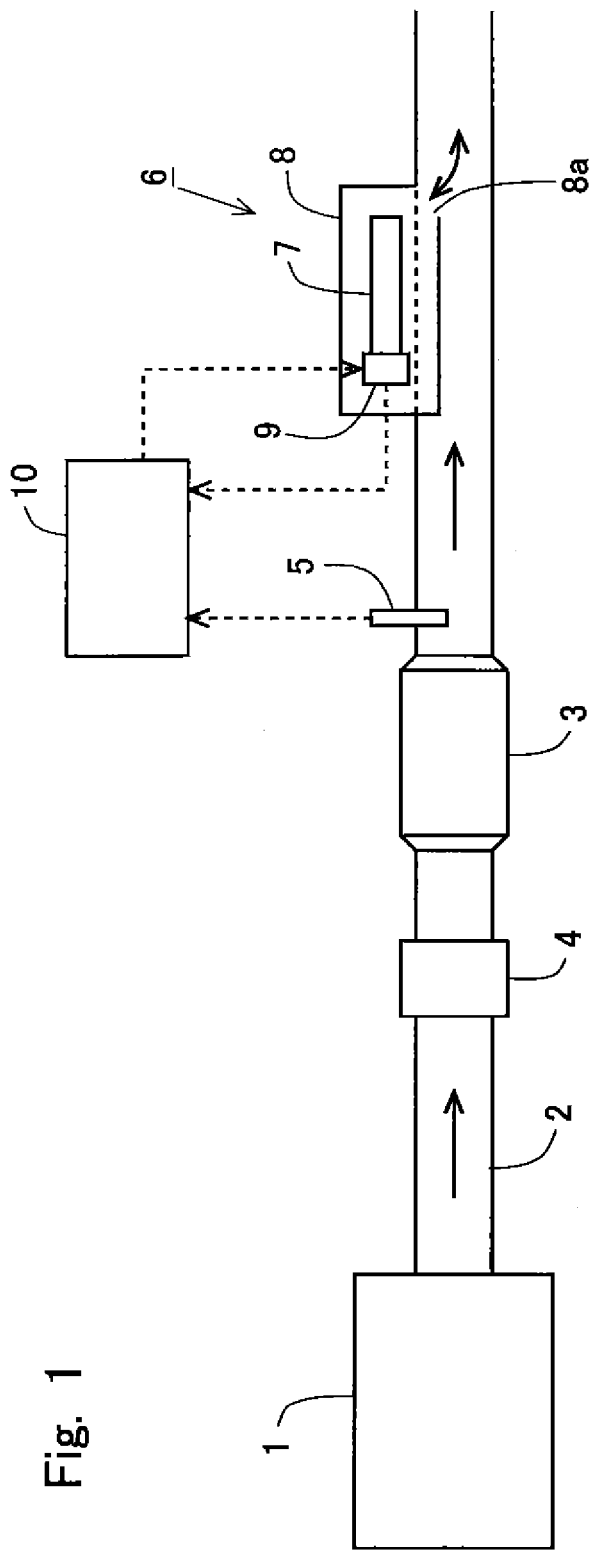
FIG. 1 shows a schematic arrangement of an exhaust system of an internal combustion engine according to a first embodiment.

FIG. 1 shows a schematic arrangement of an exhaust system of an internal combustion engine according to this embodiment. The internal combustion engine 1 is a diesel engine for driving a vehicle. An exhaust gas passage 2 is connected to the internal combustion engine 1.

A particulate filter (hereinafter referred to as "DPF") 3, which collects PM contained in an exhaust gas, is provided in the exhaust gas passage 2. An oxidation catalyst 4 is provided on the upstream side from DPF 3 in the exhaust gas passage 2. A temperature sensor 5 for detecting the temperature of the exhaust gas and a PM amount detecting apparatus 6 for detecting the PM amount contained in the exhaust gas are provided for the exhaust gas passage 2 at portions disposed on the downstream side from DPF 3 in the exhaust gas passage 2. The PM amount detecting apparatus 6 is provided with a PM sensor 7 and a sensor case 8. Details of the PM amount detecting apparatus 6 will be described later on.

An electronic control unit (ECU) 10 is provided in combination with the internal combustion engine 1. ECU 10 is a unit which controls, for example, the operation state of the internal combustion engine 1. The temperature sensor 5 and the PM sensor 7 are electrically connected to ECU 10. In addition thereto, those electrically connected to ECU 10 are various sensors including, for example, an air flow meter, a crank position sensor, and an accelerator opening degree sensor (not shown).

In this embodiment, the filter regeneration process (reproduction process), in which PM deposited or deposited in DPF 3 is oxidized and removed, is performed when a predetermined condition is established. In the filter regeneration process, the temperature of DPF 3 is raised to a target temperature at which deposited PM can be oxidized. The method for raising the temperature of DPF 3 is exemplified, for example, by a method in which the fuel is supplied to the oxidation catalyst 4 by performing the auxiliary fuel injection (sub-fuel injection) in the internal combustion engine 1, and the temperature of the exhaust gas allowed to inflow into DPF 3 is raised by using the heat of oxidation generated by the oxidation of the fuel in the oxidation catalyst 4. The temperature of DPF 3 is estimated on the basis of the detected value of the temperature sensor 5 when the filter regeneration process is executed.

Any abnormal situation, which includes, for example, the breakage and the dissolution loss, is caused in some cases due to the thermal deterioration and/or the time-dependent deterioration in DPF 3. If such an abnormal situation arises in DPF 3, the amount of PM, which outflows to the downstream side without being collected by DPF 3, is increased. In view of the above, in this embodiment, the detection of the abnormal situation of DPF 3 is carried out on the basis of the PM amount contained in the exhaust gas detected by the PM amount detecting apparatus 6. Therefore, in order to correctly detect the abnormal situation of DPF 3, it is necessary that the PM amount in the exhaust gas should be detected highly accurately by means of the PM amount detecting apparatus 6.

[Schematic Arrangement of PM Amount Detecting Apparatus]

Figure 2:
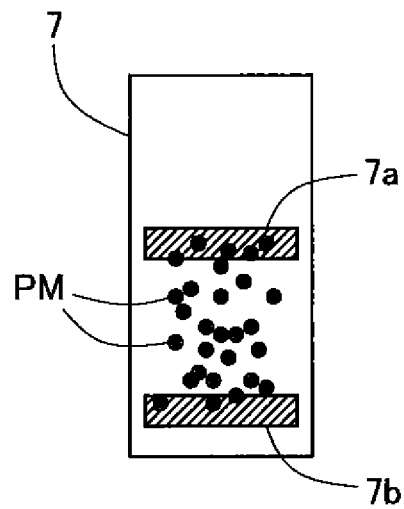
FIG. 2 shows a schematic arrangement of a PM sensor according to the first embodiment.
Figure 3:
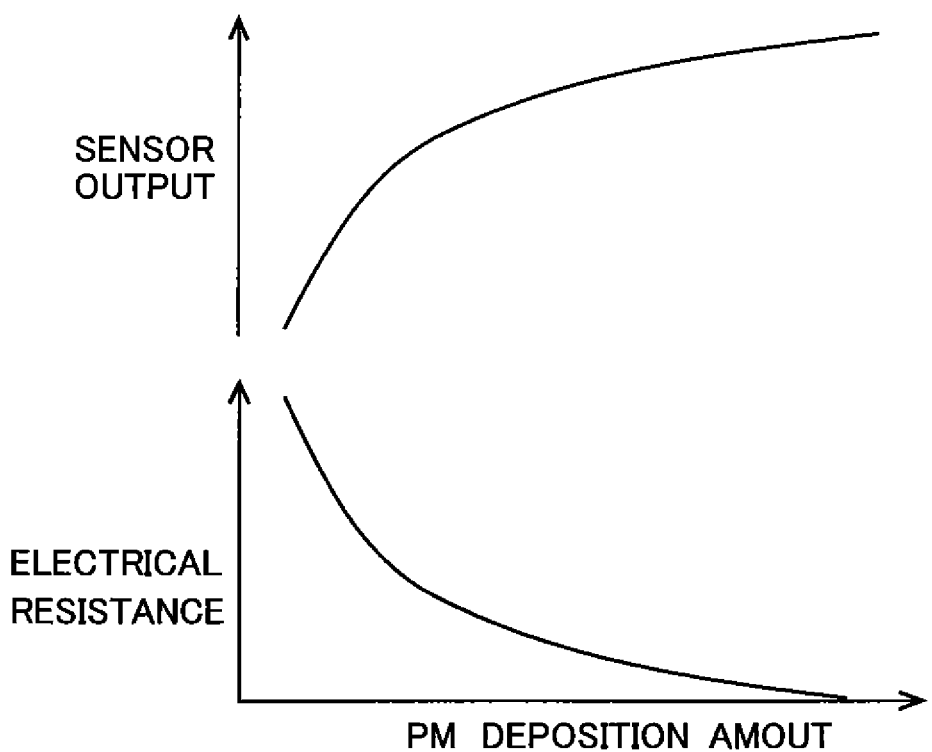
FIG. 3 shows a graph illustrating a relationship among the PM deposition amount in the PM sensor, the electrical resistance between electrodes of the PM sensor, and the output value of the PM sensor.

FIG. 2 shows a schematic arrangement of the PM sensor 7. As shown in FIG. 2, the PM sensor 7 is provided with a pair of electrodes 7a, 7b. FIG. 3 shows a graph illustrating a relationship among the PM deposition amount in the PM sensor 7, the electrical resistance between the electrodes 7a, 7b of the PM sensor 7, and the output value of the PM sensor 7. With reference to FIG. 3, the horizontal axis represents the PM deposition amount in the PM sensor 7, the vertical axis of the lower part represents the electrical resistance between the electrodes 7a, 7b of the PM sensor 7, and the vertical axis of the upper part represents the output value of the PM sensor 7.

PM in the exhaust gas adheres to the PM sensor 7, and PM is deposited between the electrodes 7a, 7b. As shown in FIG. 3, as the PM deposition amount in the PM sensor 7 is increased, the electrical resistance between the electrodes 7a, 7b is lowered. As the electrical resistance between the electrodes 7a, 7b is lowered, the output value of the PM sensor 7 is increased. Therefore, the output value of the PM sensor 7 is the value corresponding to the added-up value of the PM flow rate. Further, the PM flow rate can be also calculated by differentiating the output value of the PM sensor 7.

An electric heater 9 is provided for the PM sensor 7. If PM is excessively deposited in the PM sensor 7, it is difficult to correctly detect the PM amount in the exhaust gas on the basis of the output value thereof. In view of the above, when the PM deposition amount in the PM sensor 7 arrives at a certain amount, then the PM sensor 7 is heated by the electric heater 9, and thus PM, which is deposited in the PM sensor 7, is oxidized and removed. The electric heater 9 is electrically connected to ECU 10. The operation of the electric heater 9 is controlled by ECU 10.

The PM sensor 7 according to this embodiment is not limited to the structure or arrangement as described above. Any known PM sensor may be used as the PM sensor 7 provided that the PM sensor outputs the signal corresponding to the PM amount deposited in the sensor itself. For example, the PM amount, which is deposited in the PM sensor itself, may be estimated on the basis of the amount of increase in the temperature of the PM sensor as obtained when PM, which is deposited in the PM sensor, is combusted and removed by heating the PM sensor by means of the electric heater.

In this embodiment, the PM sensor 7 as described above is installed in the sensor case 8. In this embodiment, as shown in FIG. 1, the sensor case 8 is installed so that a part thereof is positioned in the exhaust gas passage 2, and another part is positioned outside the exhaust gas passage 2. An inlet/outlet port 8a for the exhaust gas is formed at an end portion disposed on the downstream side of a portion of the sensor case 8 positioned in the exhaust gas passage 2. A part of the exhaust gas allowed to flow through the exhaust gas passage 2 is allowed to inflow into the sensor case 8 from the inlet/outlet port 8a. The exhaust gas, which is once allowed to inflow into the sensor case 8, is allowed to outflow to the inside of the exhaust gas passage 2 from the inlet/outlet port 8a (in FIG. 1, the arrows indicate the flow of the exhaust gas). The inlet and the outlet for the exhaust gas of the sensor case 8 according to this embodiment are only the inlet/outlet port 8a. The exhaust gas, which is allowed to flow through the exhaust gas passage 2, is pulsed. Therefore, even when the inlet/outlet port 8a for the exhaust gas is formed at the end portion disposed on the downstream side of the sensor case 8, the exhaust gas can enter and exit between the exhaust gas passage 2 and the sensor case 8.

Further, as shown in FIG. 1, the PM sensor 7 is arranged at the portion positioned outside the exhaust gas passage 2 in the sensor case 8 (i.e., at the portion disposed over the broken line in the sensor case 8 as shown in FIG. 1). Further, in the sensor case 8, the PM sensor 7 is installed in such a state that the axial direction thereof is substantially parallel to the axial direction of the exhaust gas passage 2 (i.e., in such a state that the PM sensor 7 falls in the lateral direction as shown in FIG. 1).

[Effect of PM Amount Detecting Apparatus According to this Embodiment]

Figure 15:
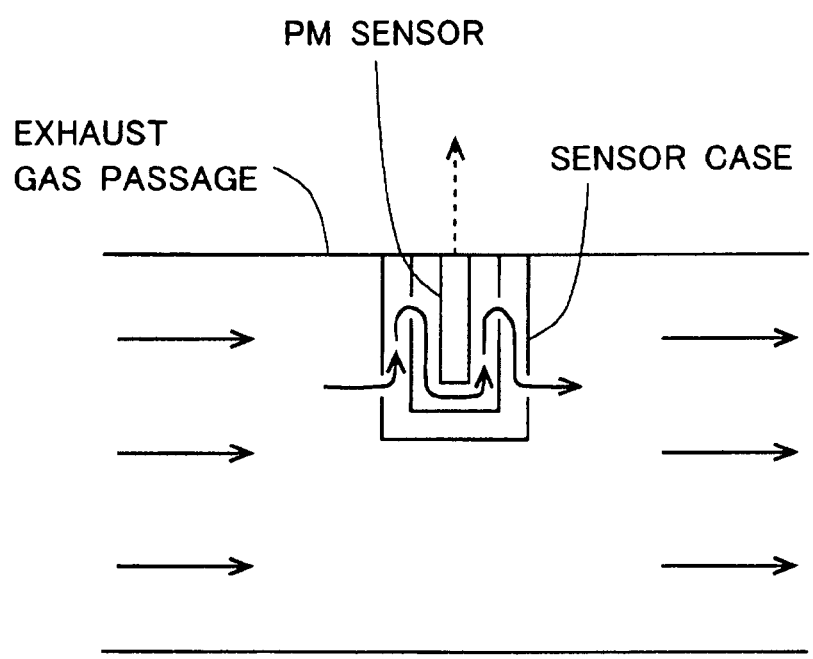
FIG. 15 shows a schematic arrangement of a conventional PM amount detecting apparatus.

An explanation will now be made about the excellent points or features of the PM amount detecting apparatus according to this embodiment as compared with a conventional case. FIG. 15 shows a schematic arrangement of a conventional PM amount detecting apparatus. Also in the case of the conventional technique, a PM sensor is installed in a sensor case in the same manner as in this embodiment. However, in the case of the conventional technique, the entire sensor case is positioned in the exhaust gas passage. Further, an exhaust gas inlet is formed on a wall surface disposed on the upstream side of the sensor case, and an exhaust gas outlet is formed on a wall surface disposed on the downstream side of the sensor case (in FIG. 15, the arrows indicate the flow of the exhaust gas).

According to the conventional structure or arrangement as described above, the flow of the exhaust gas, which is directed from the upstream side to the downstream side and which is in the same direction as that of the flow of the exhaust gas in the exhaust gas passage, is also generated in the sensor case. Therefore, a large amount of PM exists, which outflows from the sensor case without colliding against or adhering to the PM sensor even when PM inflows into the sensor case. Further, when the flow rate of the exhaust gas is raised in the exhaust gas passage, the flow rate of the exhaust gas is also raised in the sensor case. Therefore, the PM collection ratio is lowered in the PM sensor.

On the contrary, in the case of the PM amount detecting apparatus 6 according to this embodiment, the inlet/outlet port 8a for the exhaust gas is formed at only the end portion disposed on the downstream side of the sensor case 8. Accordingly, the flow rate of the exhaust gas in the sensor case 8 can be made extremely small as compared with the flow rate of the exhaust gas in the exhaust gas passage 2. Further, even when the flow rate of the exhaust gas is raised in the exhaust gas passage 2, it is possible to suppress the increase in the flow rate of the exhaust gas in the sensor case 8. That is, according to the sensor case 8 constructed as described above, the flow rate of the exhaust gas in the sensor case 8 can be lowered to such an extent that the thermal phoresis of PM can be performed as described later on.

Further, the inlet/outlet port for the exhaust gas is formed in only one direction in the sensor case 8. Accordingly, it is possible to suppress the flow of PM which is allowed to merely pass through the sensor case 8 simply without causing any collision against the PM sensor 7. Further, the inlet/outlet port is formed at the end portion disposed on the downstream side of the sensor case 8. Accordingly, PM, which exists in the sensor case B, is hardly affected by the pressure of the main flow of the exhaust gas in the exhaust gas passage 2. Therefore, the thermal phoresis of PM is performed more easily as described later on.

Further, in the PM amount detecting apparatus 6 according to this embodiment, as described above, the PM sensor 7 is installed so that the PM sensor 7 is positioned outside the exhaust gas passage 2 in the sensor case 8. The portion of the sensor case 8, which is positioned outside the exhaust gas passage 2, is cooled by the outside air. Therefore, the temperature of the PM sensor 7 is suppressed from being raised. Therefore, the temperature of the PM sensor 7 is lower than the temperature of the wall surface of the portion of the sensor case 8 positioned in the exhaust gas passage 2 (hereinafter referred to as "wall surface on the exhaust gas passage side"), and it is possible to maintain the temperature difference. When the temperature difference is generated as described above in a state in which the flow rate of the exhaust gas is sufficiently lowered in the sensor case 8, PM, which exists between the PM sensor 7 and the wall surface on the exhaust gas passage side, is guided to the PM sensor 7 in accordance with the thermal phoresis.

It is not necessarily indispensable that the PM sensor 7 should be positioned outside the exhaust gas passage 2 in the sensor case 8, provided that the temperature of the PM sensor 7 is sufficiently lower than the temperature of the wall surface on the exhaust gas passage side of the sensor case 8. Even if the PM sensor 7 is installed at the portion positioned in the exhaust gas passage 2 in the sensor case 8, when the PM sensor 7 is installed at any position disposed near to the position of the wall surface of the exhaust gas passage 2, then the temperature of the PM sensor 7 can be made sufficiently lower than the temperature of the wall surface on the exhaust gas passage side.

In the sensor case 8, the temperature difference also arises between the wall surface on the exhaust gas passage side and the wall surface (hereinafter referred to as "wall surface on the outer side") which is positioned outside the exhaust gas passage 2 and which is opposed to the wall surface on the exhaust gas passage side while interposing the PM sensor 7. That is, the temperature of the wall surface on the outer side is lower than the temperature of the wall surface on the exhaust gas passage side. Further, the temperature difference is maintained. When the temperature difference arises as described above in a state in which the flow rate of the exhaust gas is sufficiently lowered in the sensor case 8, the movement of PM also arises, which is directed from the side of the wall surface on the exhaust gas passage side to the side of the wall surface on the outer side in accordance with the thermal phoresis. In this situation, the PM sensor 7 is installed so that the axis thereof extends along the both wall surfaces. Therefore, the PM sensor 7 is positioned on the route of the movement of PM. Therefore, PM, which is moved as described above, is also guided to the PM sensor 7.

PM is guided to the PM sensor 7 in accordance with the thermal phoresis as described above, and thus it is possible to accelerate the adhesion of PM to the PM sensor 7. Therefore, according to the PM amount detecting apparatus concerning this embodiment, the PM collection ratio in the PM sensor 7 can be stably maintained to be high irrelevant to the flow rate of the exhaust gas in the exhaust gas passage 2. As a result, the PM amount in the exhaust gas can be detected more highly accurately on the basis of the output value of the PM sensor 7.

Figure 4:
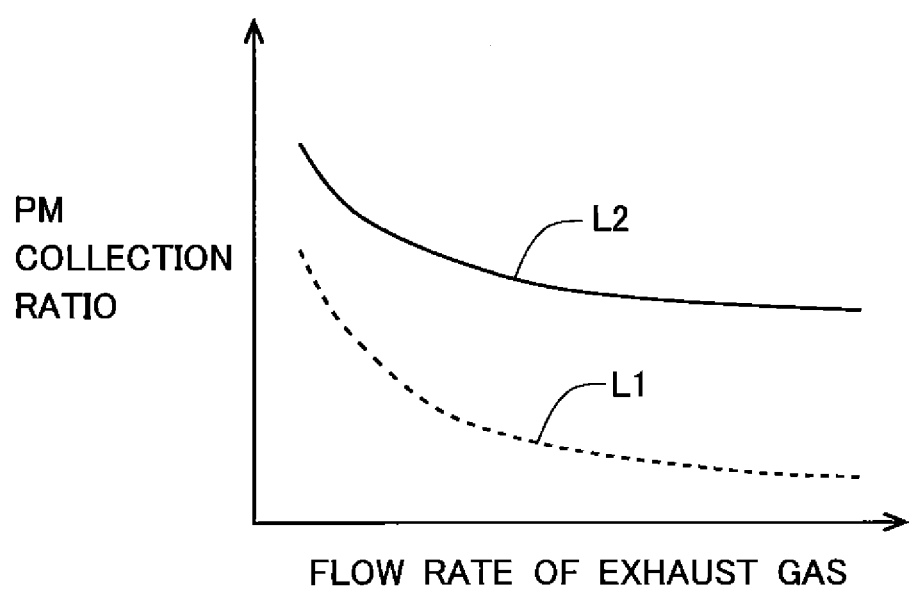
FIG. 4 shows a first graph illustrating a relationship between the flow rate of an exhaust gas in an exhaust gas passage and the PM collection ratio in the PM sensor.

FIG. 4 shows a graph illustrating a relationship between the flow rate of the exhaust gas in the exhaust gas passage and the PM collection ratio in the PM sensor. With reference to FIG. 4, a broken line L1 indicates the PM collection ratio in the conventional PM sensor shown in FIG. 15, and a solid line L2 indicates the PM collection ratio in the PM sensor according to this embodiment. As shown in FIG. 4, according to this embodiment, it is possible to improve the PM collection ratio in the PM sensor as compared with the conventional technique. In particular, when the flow rate of the exhaust gas is raised in the exhaust gas passage, it is possible to greatly improve the PM collection ratio in the PM sensor as compared with the conventional technique.

Modified Embodiments

Modified embodiments of the embodiment of the present invention will be explained with reference to FIGS. 5 to 11. Only the points or features, which are different from those of the embodiment described above, will be explained herein. In FIGS. 5 and 7 to 10, the arrows indicate the flow of the exhaust gas.

Figure 5:
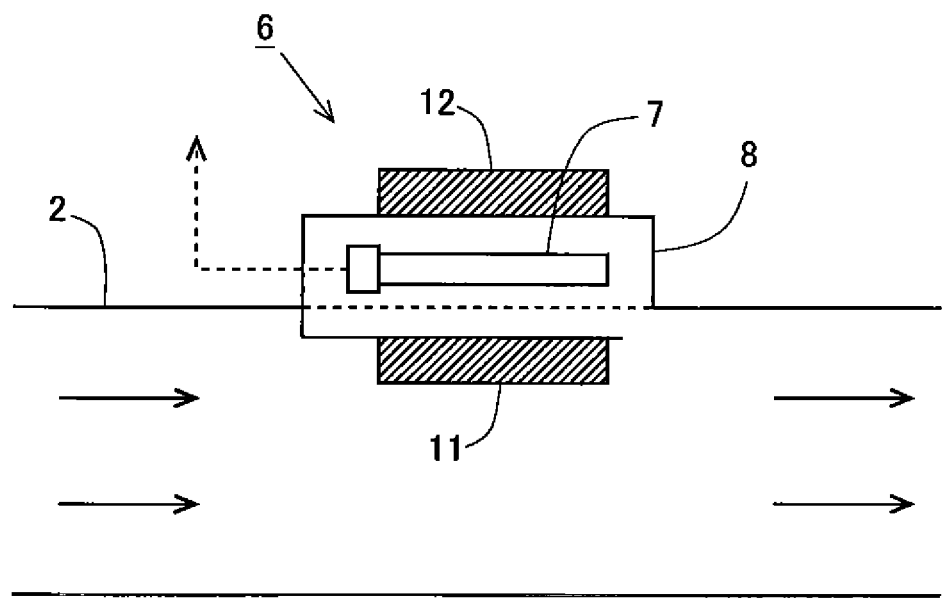
FIG. 5 shows a schematic arrangement of a PM amount detecting apparatus according to a first modified embodiment of the first embodiment.

FIG. 5 shows a schematic arrangement of a PM amount detecting apparatus according to a first modified embodiment of the embodiment of the present invention. In this modified embodiment, a heat receiving fin 11 is provided on the wall surface on the exhaust gas passage side of the sensor case 8. The heat receiving fin 11 receives the heat of the exhaust gas allowed to flow through the exhaust gas passage 2. Accordingly, it is possible to accelerate the heating of the wall surface on the exhaust gas passage side of the sensor case 8 by means of the exhaust gas.

Further, a heat releasing fin 12 is provided on the wall surface on the outer side of the sensor case 8. The heat releasing fin 12 releases the heat of the exhaust gas contained in the sensor case 8 to the outside. Accordingly, it is possible to accelerate the cooling of the wall surface on the outer side of the sensor case 8 by means of the outside air. It is also allowable to enhance the cooling effect on the wall surface on the outer side of the sensor case 8 by performing the heat exchange, for example, with cooling water.

According to this modified embodiment, it is possible to further increase the temperature difference between the PM sensor 7 and the wall surface on the exhaust gas passage side of the sensor case 8 and the temperature difference between the wall surface on the outer side and the wall surface on the exhaust gas passage side of the sensor case 8. As a result, it is possible to accelerate the guided movement (introduction or induction) of PM to the PM sensor 7 by means of the thermal phoresis.

Figure 6:
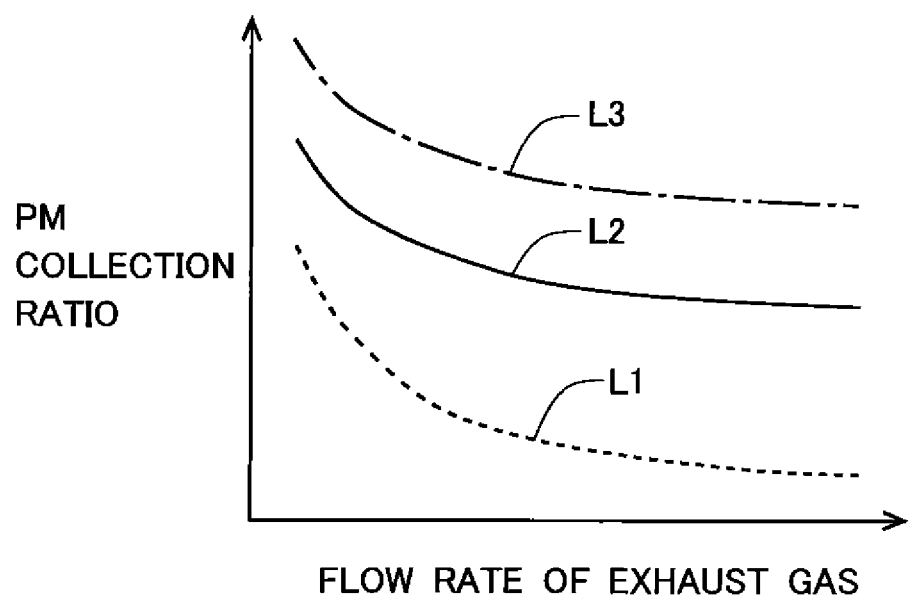
FIG. 6 shows a second graph illustrating a relationship between the flow rate of an exhaust gas in an exhaust gas passage and the PM collection ratio in a PM sensor.

FIG. 6 shows a graph illustrating a relationship between the flow rate of the exhaust gas in the exhaust gas passage and the PM collection ratio in the PM sensor. With reference to FIG. 6, a broken line L1 indicates the PM collection ratio in the conventional PM sensor shown in FIG. 15, a solid line L2 indicates the PM collection ratio in the PM sensor according to the embodiment described above, and an alternate long and short dash line L3 indicates the PM collection ratio in the PM sensor according to this modified embodiment. As shown in FIG. 6, according to this modified embodiment, the PM collection ratio can be further improved in the PM sensor 7 as compared with the cases in which the heat receiving fin 11 and the heat releasing fin 12 are not provided for the sensor case 8.

It is not necessarily indispensable that both of the heat receiving fin 11 and the heat releasing fin 12 should be provided for the sensor case 8. Even when only any one of the heat receiving fin 11 and the heat releasing fin 12 is provided for the sensor case 8, it is possible to increase the temperature difference between the PM sensor 7 and the wall surface on the exhaust gas passage side of the sensor case 8 and the temperature difference between the wall surface on the outer side and the wall surface on the exhaust gas passage side of the sensor case 8, as compared with the structure or arrangement in which the fin 11, 12 is not provided.

Figure 7:
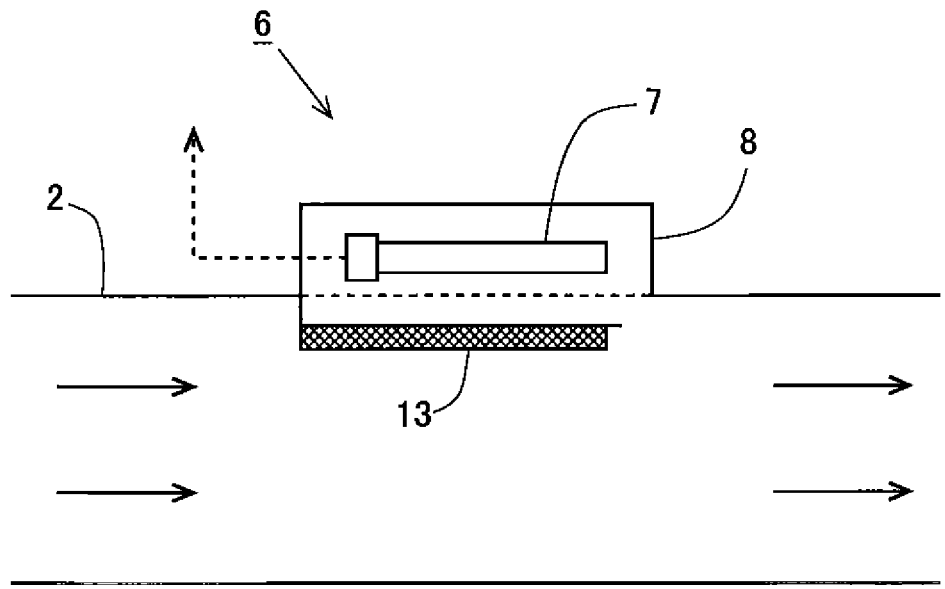
FIG. 7 shows a schematic arrangement of a PM amount detecting apparatus according to a second modified embodiment of the first embodiment.

FIG. 7 shows a schematic arrangement of a PM amount detecting apparatus according to a second modified embodiment of the embodiment of the present invention. In this modified embodiment, a catalyst 13 is provided on the outer side of the wall surface on the exhaust gas passage side of the sensor case 8. The catalyst 13 is a catalyst (for example, an oxidation catalyst) which has the oxidation function. The fuel component (HC) contained in the exhaust gas, which is allowed to flow through the exhaust gas passage 2, is oxidized on the catalyst 13. The heating of the wall surface on the exhaust gas passage side of the sensor case 8 is accelerated by the heat of oxidation generated in this situation.

According to this modified embodiment, it is also possible to further increase the temperature difference between the PM sensor 7 and the wall surface on the exhaust gas passage side of the sensor case 8 and the temperature difference between the wall surface on the outer side and the wall surface on the exhaust gas passage side of the sensor case 8 in the same manner as in the first modified embodiment. As a result, it is possible to accelerate the guided movement (introduction or induction) of PM to the PM sensor 7 in accordance with the thermal phoresis. Therefore, it is possible to further improve the PM collection ratio in the PM sensor 7 as compared with the case in which the catalyst 13 is not provided for the sensor case 8.

Figure 8:
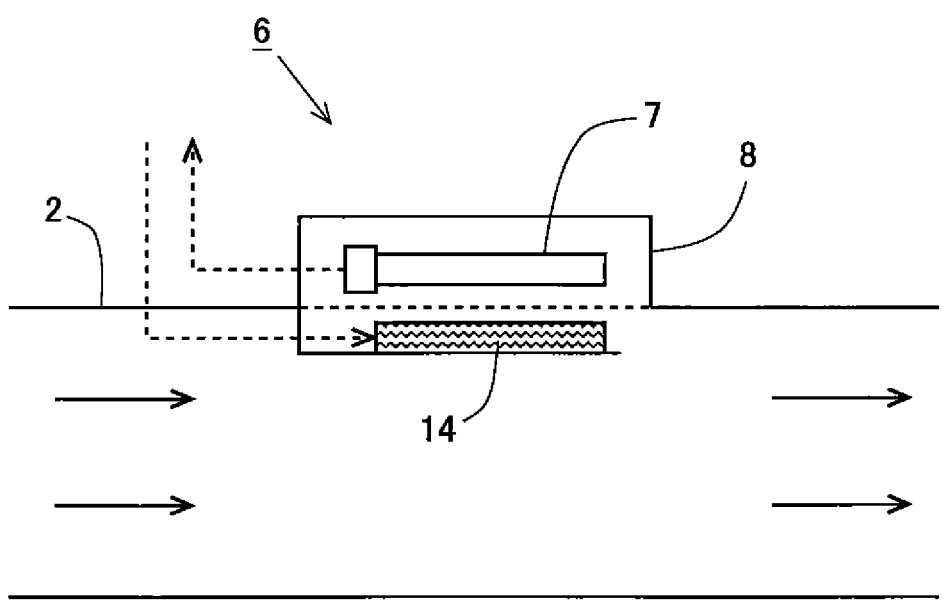
FIG. 8 shows a schematic arrangement of a PM amount detecting apparatus according to a third modified embodiment of the first embodiment.

FIG. 8 shows a schematic arrangement of a PM amount detecting apparatus according to a third modified embodiment of the embodiment of the present invention. In this modified embodiment, an electric heater 14 is provided, which heats the wall surface on the exhaust gas passage side of the sensor case 8. The electric heater 14 is electrically connected to ECU 10. The operation of the electric heater 14 is controlled by ECU 10.

According to this modified embodiment, it is also possible to further increase the temperature difference between the PM sensor 7 and the wall surface on the exhaust gas passage side of the sensor case 8 and the temperature difference between the wall surface on the outer side and the wall surface on the exhaust gas passage side of the sensor case 8 in the same manner as in the first and second modified embodiments, by heating the wall surface on the exhaust gas passage side by means of the electric heater 14. As a result, it is possible to accelerate the guided movement (introduction or induction) of PM to the PM sensor 7 in accordance with the thermal phoresis. Therefore, it is possible to further improve the PM collection ratio in the PM sensor 7 as compared with the case in which the electric heater 14 is not provided for the sensor case 8.

In the second and third modified embodiments, it is also allowable to provide a heat releasing fin on the wall surface on the outer side of the sensor case 8 in the same manner as in the first modified embodiment. Accordingly, it is possible to further increase the temperature difference in the sensor case 8 as described above.

Figure 9:
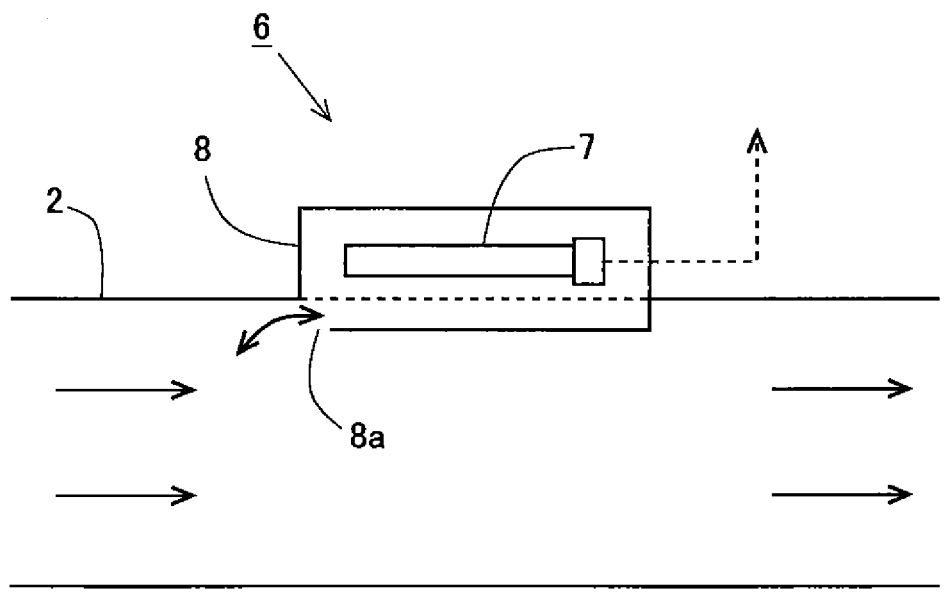
FIG. 9 shows a first drawing illustrating a schematic arrangement of a PM amount detecting apparatus according to a fourth modified embodiment of the first embodiment.
Figure 10:
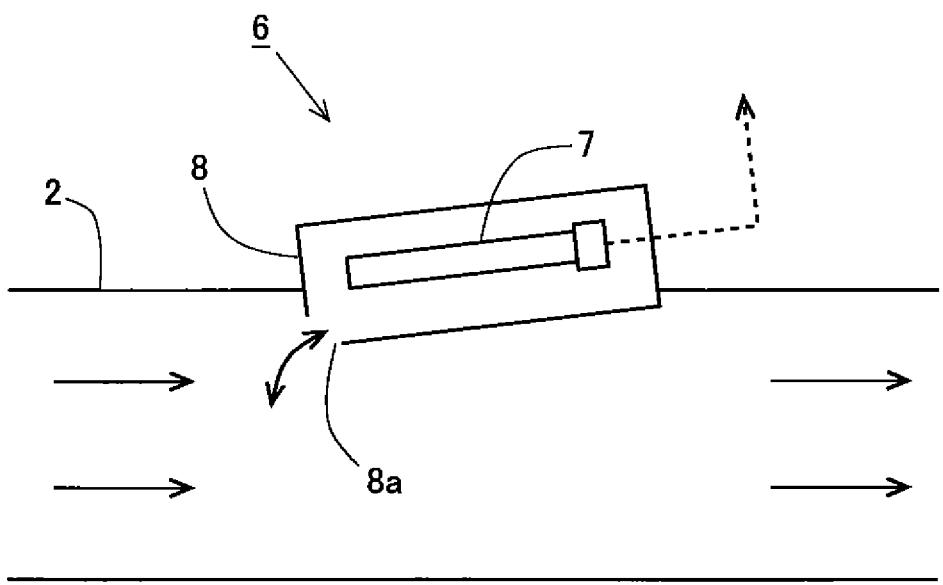
FIG. 10 shows a second drawing illustrating a schematic arrangement of a PM amount detecting apparatus according to the fourth modified embodiment of the first embodiment.
Figure 11:
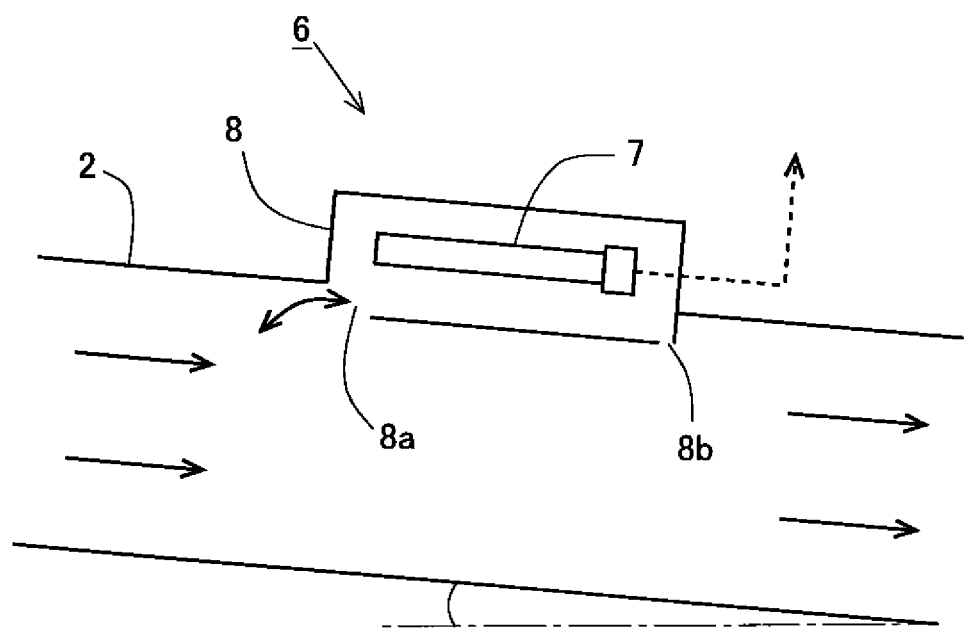
FIG. 11 shows a third drawing illustrating a schematic arrangement of a PM amount detecting apparatus according to the fourth modified embodiment of the first embodiment.

FIGS. 9 to 11 show schematic arrangements of PM amount detecting apparatuses according to a fourth modified embodiment of the embodiment of the present invention. In this modified embodiment, as shown in FIG. 9, an inlet/outlet port 8a for the exhaust gas is formed at an end portion on the upstream side of a portion of the sensor case 8 positioned in the exhaust gas passage 2. In the sensor case 8 according to this modified embodiment, the inlet and the outlet for the exhaust gas are only the inlet/outlet port 8a.

Even in the case of the arrangement as described above, the exhaust gas, which inflows from the inlet/outlet port 8a into the sensor case 8, is suppressed from passing through the inside of the sensor case 8 as it is and outflowing into the exhaust gas passage 2 from the downstream side of the sensor case 8. Therefore, the flow rate of the exhaust gas in the sensor case 8 can be decreased as compared with the flow rate of the exhaust gas in the exhaust gas passage 2 in the same manner as in the case in which the inlet/outlet port 8a for the exhaust gas is formed at the end portion on the downstream side of the sensor case 8. Further, even when the flow rate of the exhaust gas is raised in the exhaust gas passage 2, it is possible to suppress the increase in the flow rate of the exhaust gas in the sensor case 8. That is, the flow rate of the exhaust gas in the sensor case 8 can be lowered to such an extent that the thermal phoresis of PM can be performed. Further, it is possible to suppress the flow of PM which merely passes through the inside of the sensor case 8 simply without colliding with the PM sensor 7.

When the inlet/outlet port 8a for the exhaust gas is formed at the end portion on the upstream side of the portion of the sensor case 8 positioned in the exhaust gas passage 2 as in this modified embodiment, as shown in FIG. 10, the sensor case 8 may be installed while being inclined toward the upstream side (i.e., the position of the end portion on the upstream side is lower than the position of the end portion on the downstream side). Accordingly, when any condensed water is produced in the sensor case 8, the condensed water can be discharged from the inlet/outlet port 8a for the exhaust gas.

Further, as shown in FIG. 11, the sensor case 8 is sometimes in a state in which the sensor case 8 is inclined toward the downstream side as well, because the exhaust gas passage 2 is in an inclined state when the vehicle, which carries the internal combustion engine 1, runs on the level ground or in the flat area, depending on the position of installation of the PM amount detecting apparatus 6 in the exhaust gas passage 2 (i.e., the position of the end portion on the upstream side is higher than the position of the end portion on the downstream side). In such a situation, a discharge port 8b, which is usable to discharge the condensed water from the inside of the sensor case 8, may be provided at an end portion on the downstream side of a portion of the sensor case 8 positioned in the exhaust gas passage 2.

In this arrangement, the size of the discharge port 8b is made extremely small as compared with the inlet/outlet port 8a for the exhaust gas, in order to suppress the outflow of the exhaust gas from the discharge port 8b into the exhaust gas passage 2. Accordingly, it is possible to suppress the increase in the flow rate of the exhaust gas in the sensor case 8, which would be otherwise caused by the provision of the discharge port 8b for the sensor case 8.

Second Embodiment

A second embodiment of the present invention will be explained on the basis of FIG. 12. Only the points or features, which are different from those of the first embodiment, will be explained herein.

Figure 12:
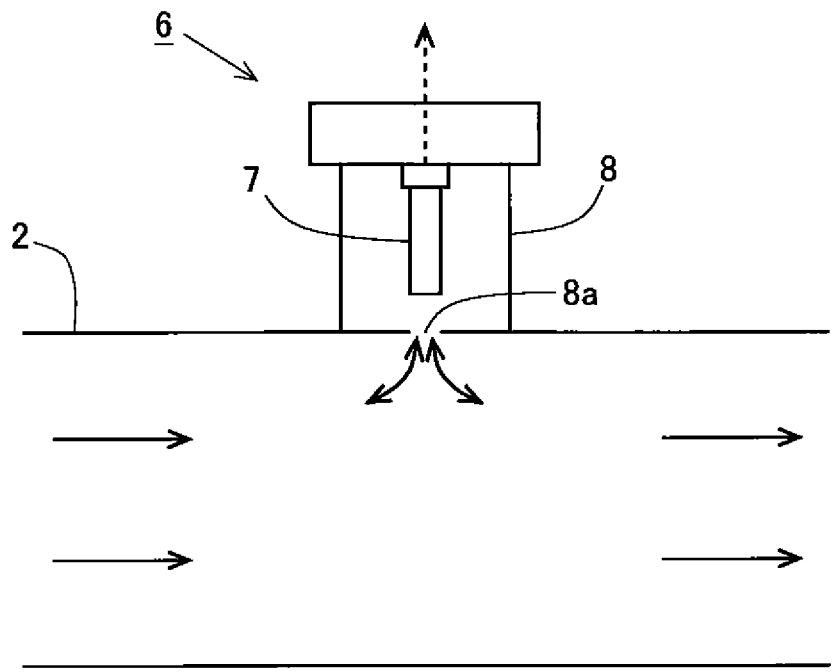
FIG. 12 shows a schematic arrangement of a PM amount detecting apparatus according to a second embodiment.

FIG. 12 shows a schematic arrangement of a PM amount detecting apparatus according to this embodiment. As shown in FIG. 12, in this embodiment, the PM amount detecting apparatus 6 is provided outside the exhaust gas passage 2. That is, an entire sensor case 8 is positioned outside the exhaust gas passage 2. Further, the wall surface of the sensor case 8, which is disposed on the side of the exhaust gas passage 2, is brought in contact with the outer wall of the exhaust gas passage 2. Further, an inlet/outlet port 8a for the exhaust gas is formed at a portion of the wall surface of the sensor case 8 brought in contact with the outer wall of the exhaust gas passage 2 (in FIG. 12, the arrows indicate the flow of the exhaust gas). The PM sensor 7 is installed in the sensor case 8 in such a state that the axial direction thereof intersects the axial direction of the exhaust gas passage 2 substantially perpendicularly.

Even when the PM amount detecting apparatus 6 is constructed as described above, any one of the exhaust gas allowed to inflow into the sensor case 8 and the exhaust gas allowed to outflow from the sensor case 8 passes through the inlet/outlet port 8a. Therefore, the flow rate of the exhaust gas in the sensor case 8 can be made smaller than the flow rate of the exhaust gas in the exhaust gas passage 2 in the same manner as in the PM amount detecting apparatus according to the first embodiment. Further, even when the flow rate of the exhaust gas is raised in the exhaust gas passage 2, it is possible to suppress the increase in the flow rate of the exhaust gas in the sensor case 8. That is, it is possible to lower the flow rate of the exhaust gas in the sensor case 8 to such an extent that the thermal phoresis of PM can be performed. Further, the flow of PM, which merely passes through the inside of the sensor case 8 simply without colliding against the PM sensor 7, is suppressed.

Further, in this embodiment, the direction of the main flow of the exhaust gas in the exhaust gas passage 2 is different from the direction of the flow of the exhaust gas allowed to inflow into the sensor case 8. Therefore, PM, which exists in the sensor case 8, is hardly affected by the pressure of the main flow of the exhaust gas in the exhaust gas passage 2.

Also in this embodiment, the PM sensor 7 is positioned outside the exhaust gas passage 2. Therefore, the increase in the temperature of the PM sensor 7 is suppressed. Therefore, the temperature of the PM sensor 7 is lower than the temperature of the wall surface of the portion of the sensor case 8 brought in contact with the exhaust gas passage 2, and it is possible to maintain the temperature difference.

Therefore, also in the PM amount detecting apparatus according to this embodiment, PM is guided to the PM sensor in accordance with the thermal phoresis in the sensor case 8. Therefore, the PM collection ratio can be stably maintained to be high in the PM sensor 7 irrelevant to the flow rate of the exhaust gas in the exhaust gas passage 2.

Third Embodiment

A third embodiment of the present invention will be explained on the basis of FIGS. 13 and 14. Only the points or features, which are different from those of the second embodiment, will be explained herein.

Figure 13:
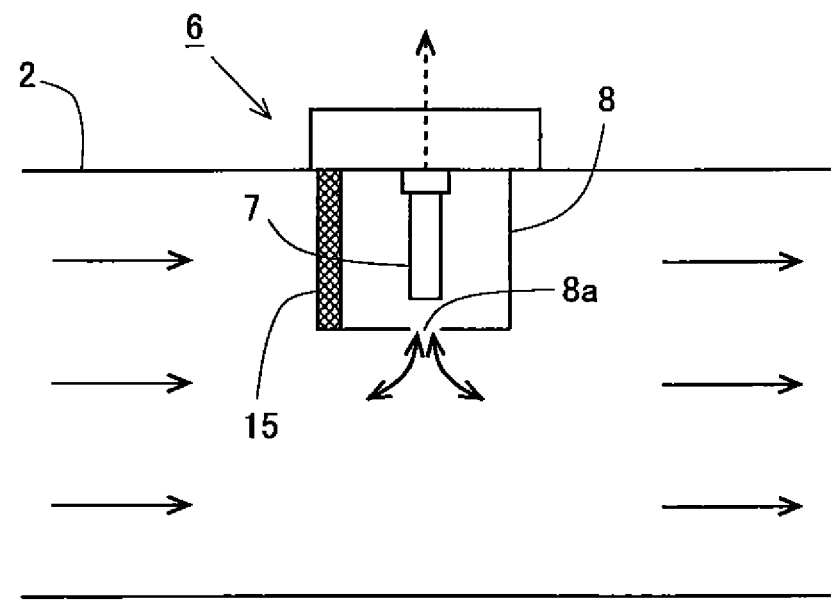
FIG. 13 shows a schematic arrangement of a PM amount detecting apparatus according to a third embodiment.

FIG. 13 shows a schematic arrangement of a PM amount detecting apparatus according to this embodiment. As shown in FIG. 13, in this embodiment, the PM amount detecting apparatus 6 is provided inside the exhaust gas passage 2. That is, an entire sensor case 8 is positioned inside the exhaust gas passage 2. The wall surface of the sensor case 8, which is disposed on the side of the inner wall of the exhaust gas passage 2, is brought in contact with the inner wall of the exhaust gas passage 2. An inlet/outlet port 8a for the exhaust gas is formed at the wall surface of the sensor case 8 opposed to the wall surface brought in contact with the inner wall of the exhaust gas passage 2 (in FIG. 13, the arrows indicate the flow of the exhaust gas).

A catalyst 15 is provided on the outer side of the wall surface on the upstream side of the sensor case 8. The catalyst 15 is a catalyst (for example, an oxidation catalyst) which has the oxidation function. The fuel component (HC) contained in the exhaust gas, which is allowed to flow through the exhaust gas passage 2, is oxidized on the catalyst 15. The heating of the wall surface on the upstream side of the sensor case 8 is accelerated by the heat of oxidation generated in this situation.

According to the structure or arrangement as described above concerning this embodiment, it is also possible to lower the flow rate of the exhaust gas in the sensor case 8 to such an extent that the thermal phoresis of PM can be performed, for the same reason as that referred to in the second embodiment. Further, the flow of PM, which merely passes through the inside of the sensor case 8 simply without colliding against the PM sensor 7, is suppressed. Further, PM, which exists in the sensor case B, is hardly affected by the pressure of the main flow of the exhaust gas in the exhaust gas passage 2.

The wall surface on the upstream side of the sensor case 8 is heated by the heat of oxidation generated by the catalyst 15, and thus the temperature difference arises between the wall surface and the PM sensor 7. That is, the temperature of the PM sensor 7 is lower than the temperature of the wall surface on the upstream side of the sensor case 8, and the temperature difference can be maintained. Further, the temperature difference also arises between the wall surface on the upstream side and the wall surface on the downstream side opposed to the wall surface on the upstream side while interposing the PM sensor 7 in the sensor case 8, and the temperature difference can be maintained.

Therefore, also in the PM amount detecting apparatus according to this embodiment, PM is guided to the PM sensor in accordance with the thermal phoresis in the sensor case 8. Therefore, the PM collection ratio can be stably maintained to be high in the PM sensor 7 irrelevant to the flow rate of the exhaust gas in the exhaust gas passage 2.

In this embodiment, a cooling device, which cools the wall surface by means of the heat exchange with cooling water or the like, may be further provided for the wall surface on the downstream side of the sensor case 8. Accordingly, it is possible to further increase the temperature difference between the wall surface on the upstream side and the wall surface on the downstream side opposed thereto while interposing the PM sensor 7. Therefore, it is possible to further accelerate the guided movement (introduction or induction) of PM to the PM sensor 7 in accordance with the thermal phoresis.

Modified Embodiment

Figure 14:
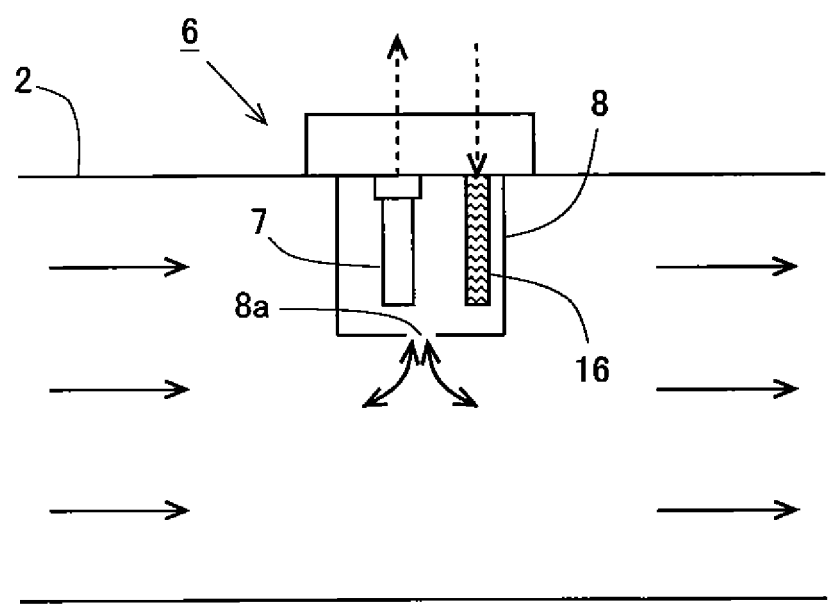
FIG. 14 shows a schematic arrangement of a PM amount detecting apparatus according to a modified embodiment of the third embodiment.

FIG. 14 shows a schematic arrangement of a PM amount detecting apparatus according to a modified embodiment of the embodiment of the present invention. As shown in FIG. 14, in this modified embodiment, an electric heater 16, which heats a part of the wall surface of the sensor case 8, may be provided in the sensor case 8 in place of the catalyst 15. The electric heater 16 is electrically connected to ECU 10. The operation of the electric heater 16 is controlled by ECU 10.

When the part of the wall surface of the sensor case 8 is heated by the electric heater 16, then the temperature difference can be generated in the same manner as in the embodiment described above between the wall surface and the PM sensor 7 and between the wall surfaces opposed to one another while interposing the PM sensor 7 in the sensor case 8, and the temperature difference can be maintained.

Also in this modified embodiment, a cooling device, which cools the wall surface by means of the heat exchange with cooling water or the like, may be further provided for the wall surface opposed to the wall surface heated by the electric heater 16 while interposing the PM sensor 7 in the sensor case 8. Accordingly, it is possible to further increase the temperature difference between the wall surfaces opposed to one another while interposing the PM sensor 7 in the sensor case 8.

The respective embodiments described above can be combined with each other as far as possible.

DESCRIPTION OF THE REFERENCE SIGNS

1: internal combustion engine
2: exhaust gas passage
3: particulate filter
4: oxidation catalyst
5: temperature sensor
6: PM amount detecting apparatus
7: PM sensor
7a, 7b: electrode
8: sensor case
9, 14, 16: electric heater
10: ECU
11: heat receiving fin
12: heat releasing fin
13, 15: catalyst

The invention claimed is:

1. A PM amount detecting apparatus which is provided for an exhaust gas passage of an internal combustion engine and which detects an amount of particulate matter contained in an exhaust gas, the PM amount detecting apparatus comprising:
a PM sensor which outputs a signal corresponding to the amount of the particulate matter deposited in the PM sensor itself; and
a sensor case which includes the PM sensor installed therein and into which a part of the exhaust gas allowed to flow through the exhaust gas passage is taken, the sensor case having a structure which lowers a flow rate of the exhaust gas therein to such an extent that the particulate matter is capable of performing thermal phoresis, and a structure which generates therein such a temperature difference that the particulate matter is guided to the PM sensor in accordance with the thermal phoresis, wherein the sensor case has such a structure that the temperature difference is generated between wall surfaces which are opposed to one another while interposing the PM sensor.

2. The PM amount detecting apparatus according to claim 1, wherein the sensor case has an inlet/outlet port for the exhaust gas which is formed in only one direction.

3. The PM amount detecting apparatus according to claim 2, wherein the inlet/outlet port for the exhaust gas is formed at only an end portion of the sensor case disposed on a downstream side.

4. A PM amount detecting apparatus which is provided for an exhaust gas passage of an internal combustion engine and which detects an amount of particulate matter contained in an exhaust gas, the PM amount detecting apparatus comprising:
 a PM sensor which outputs a signal corresponding to the amount of the particulate matter deposited in the PM sensor itself; and
 a sensor case which includes the PM sensor installed therein and into which a part of the exhaust gas allowed to flow through the exhaust gas passage is intaken, the sensor case having a structure which lowers a flow rate of the exhaust gas therein to such an extent that the particulate matter is capable of performing thermal phoresis, and a structure which generates therein such a temperature difference that the particulate matter is guided to the PM sensor in accordance with the thermal phoresis, wherein:
 the sensor case is installed so that a part thereof is positioned in the exhaust gas passage and another part is positioned outside the exhaust gas passage; and
 the PM sensor is arranged at a portion which is positioned outside the exhaust gas passage in the sensor case or at a portion which is positioned in the exhaust gas passage in the sensor case in the vicinity of a position of a wall surface of the exhaust gas passage.

5. The PM amount detecting apparatus according to claim 4, wherein the sensor case has at least any one of a heating device which heats a wall surface of a portion of the sensor case positioned in the exhaust gas passage and a cooling device which cools a wall surface of a portion of the sensor case positioned outside the exhaust gas passage.

6. The PM amount detecting apparatus according to claim 5, wherein the heating device is a heat receiving fin which receives heat of the exhaust gas allowed to flow through the exhaust gas passage, and the cooling device is a heat releasing fin which releases heat of the exhaust gas in the sensor case to outside.

7. The PM amount detecting apparatus according to claim 4, wherein the sensor case has an inlet/outlet port for the exhaust gas which is formed in only one direction.

8. The PM amount detecting apparatus according to claim 7, wherein the inlet/outlet port for the exhaust gas is formed at only an end portion of the sensor case disposed on a downstream side.

9. A PM amount detecting apparatus which is provided for an exhaust gas passage of an internal combustion engine and which detects an amount of particulate matter contained in an exhaust gas, the PM amount detecting apparatus comprising:
 a PM sensor which outputs a signal corresponding to the amount of the particulate matter deposited in the PM sensor itself; and
 a sensor case which includes the PM sensor installed therein and into which a part of the exhaust gas allowed to flow through the exhaust gas passage is intaken, the sensor case having a structure which lowers a flow rate of the exhaust gas therein to such an extent that the particulate matter is capable of performing thermal phoresis, and a structure which dictates therein such a temperature difference that the particulate matter is guided to the PM sensor in accordance with the thermal phoresis,
 wherein the sensor case is installed so that at least a part thereof is positioned in the exhaust gas passage, and the apparatus includes a catalyst which has an oxidation function and which is provided at a portion positioned in the exhaust gas passage, the portion being a part of an outer wall surface of the sensor case.

10. The PM amount detecting apparatus according to claim 9, wherein the sensor case has an inlet/outlet port for the exhaust gas which is formed in only one direction.

11. The PM amount detecting apparatus according to claim 10, wherein the inlet/outlet port for the exhaust gas is formed at only an end portion of the sensor case disposed on a downstream side.

12. A PM amount detecting apparatus which is provided for an exhaust gas passage of an internal combustion engine and which detects an amount of particulate matter contained in an exhaust gas, the PM amount detecting apparatus comprising:
 a PM sensor which outputs a signal corresponding to the amount of the particulate matter deposited in the PM sensor itself; and
 a sensor case which includes the PM sensor installed therein and into which a part of the exhaust gas allowed to flow through the exhaust gas passage is intaken, the sensor case having a structure which lowers a flow rate of the exhaust gas therein to such an extent that the particulate matter is capable of performing thermal phoresis, and a structure which generates therein such a temperature difference that the particulate matter is guided to the PM sensor in accordance with the thermal phoresis,
 wherein the sensor case has a heating device which heats a part of a wall surface of the sensor case.

13. The PM amount detecting apparatus according to claim 12, wherein the sensor case further includes a cooling device which cools a portion of the wall surface of the sensor case opposed to a portion heated by the heating device while interposing the PM sensor.

14. The PM amount detecting apparatus according to claim 12, wherein the sensor case has an inlet/outlet port for the exhaust gas which is formed in only one direction.

15. The PM amount detecting apparatus according to claim 14, wherein the inlet/outlet port for the exhaust gas is formed at only an end portion of the sensor case disposed on a downstream side.

* * * * *